United States Patent [19]
Berglund et al.

[11] Patent Number: 5,939,382
[45] Date of Patent: Aug. 17, 1999

[54] REDUCING AGENT FOR REDUCTIVE ALKYLATION OF GLYCOPEPTIDE ANTIBIOTICS

[75] Inventors: Richard Alan Berglund; Hua Zheng, both of Lafayette, Ind.

[73] Assignee: Eli Lilly and Company, Indianapolis, Ind.

[21] Appl. No.: 08/968,320

[22] Filed: Nov. 12, 1997

Related U.S. Application Data

[60] Provisional application No. 60/031,595, Nov. 21, 1996.
[51] Int. Cl.$^6$ .......................... A61K 38/12; A61K 38/14; C07K 9/00
[52] U.S. Cl. .................................. 514/8; 514/9; 530/317; 530/322; 530/323; 530/345
[58] Field of Search ........................... 514/8, 9; 530/317, 530/322, 323, 345

[56] References Cited

U.S. PATENT DOCUMENTS

| | | | |
|---|---|---|---|
| 4,698,327 | 10/1987 | Nagarajan et al. | 514/8 |
| 4,877,450 | 10/1989 | Brasch | 106/1.26 |
| 5,591,714 | 1/1997 | Nagarajan et al. | 514/9 |

FOREIGN PATENT DOCUMENTS

| | | | |
|---|---|---|---|
| 0 435 503 A1 | 7/1991 | European Pat. Off. | C07K 9/00 |
| 0 667 353 A1 | 8/1995 | European Pat. Off. | C07K 9/00 |

OTHER PUBLICATIONS

Stults, N.L., et al., *Anal. Biochem.,* 180, 114–119 (1989).
Bomann, M.D., et al., *J. Org. Chem.,* 60, 5995–5996 (1995).
Pelter, A., et al., *J. Chem. Soc.,* Perkin Trans. 1, 717–720 (1984).
Wong, W.S.D., et al., *Anal. Biochem.,* 139, 58–67 (1984).
Nagabhushan, T.L. et al., *Carbohydrate Research,* 130, 243–249 (1984).
Nagarajan, R., et al., *J. of Antibiotics,* XLII, No. 1, 63–72 (Jan. 1989).
Cooper, R.D.G., et al., *J. of Antibiotics,* 49, No. 6, 575–581 (Jun. 1996).
Lee, R.T., et al., *Biochemistry,* 28, 1856–1861 (1989).

*Primary Examiner*—Frederick Krass
*Attorney, Agent, or Firm*—Arlene K. Musser

[57] ABSTRACT

This invention is concerned with improved processes for reductive alkylation of glycopeptide antibiotics, the improvement residing in employing pyridine.borane as reducing agent.

12 Claims, No Drawings

REDUCING AGENT FOR REDUCTIVE ALKYLATION OF GLYCOPEPTIDE ANTIBIOTICS

CROSS-REFERENCE

This application claims the benefit of U.S. Provisional Application No. 60/031,595, filed Nov. 21, 1996.

BRIEF SUMMARY

The present invention is directed to improved methods for reductively alkylating glycopeptide antibiotics, the improvement residing in the use of pyridine.borane complex as the reducing agent.

DETAILED DESCRIPTION

The present invention relates to reductive alkylation of glycopeptide antibiotics.

The glycopeptide antibiotics are a large class of substances either produced by microorganisms, or produced by microorganisms and thereafter subsequently modified in part. Two of these, vancomycin and teicoplanin, are sold as antibacterial products, but many others have been discovered and are being considered for development, especially since the emergence in the late 1980s of resistance to various antibiotics, including the glycopeptides themselves. The entire class of glycopeptide antibiotics is well described in "Glycopeptide Antibiotics", edited by Ramakrishnan Nagarajan (Marcel Dekker, Inc., New York, 1994). Among the more recently discovered glycopeptides are those known as A82846A (also called ereomomycin), A82846B (also known as chloroorienticin A), A82846C (also known as orienticin C), and orienticin A. The present invention is preferred for use with vancomycin type glycopeptide antibiotics, including vancomycin, A82846A, A82846B, A82846C, and orienticin A. The invention is especially preferred for use with A82846B.

Many modifications of naturally-occurring glycopeptides have been made. Among the modifications are reductive alkylations of reactive amine(s) in glycopeptides. See, for example, U.S. Pat. No. 4,698,327 describing reductive alkylations of vancomycin, and EPO 435 503 A1 and EPO 667 353 A1, both of which describe reductive alkylations of a variety of glycopeptides including vancomycin, A82846A, A82846B, A82846C, and orienticin A. These references describe reductive alkylations which introduce into the parent glycopeptides a great variety of alkyl groups.

U.S. Pat. No. 4,698,327 describes alkylated vancomycin compounds of the formula:

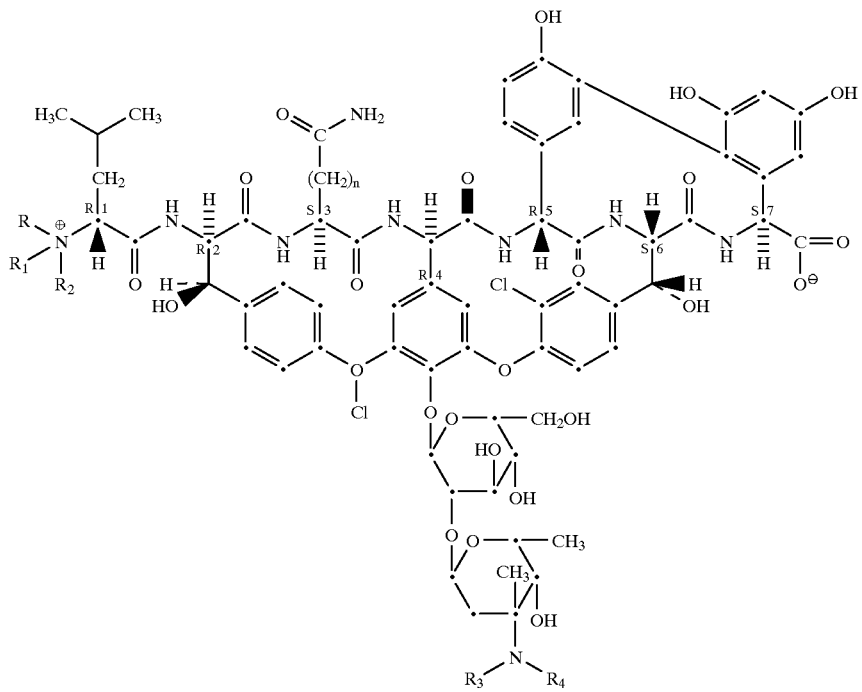

wherein
R is hydrogen or methyl;
n is 1 or 2; and
$R_1$ is hydrogen or methyl;
$R_2$ and $R_3$, independently, are hydrogen or a group of the formula: $R_6R_7CH-$;
$R_6$ and $R_7$ are independently $R_5$, $R_5-(C_1-C_5\text{-alkyl})$ or $R_5-(C_2-C_5\text{-alkenyl})$;
$R_5$ is hydrogen, $C_1-C_{10}$-alkyl, $C_2-C_{10}$-alkenyl, $C_1-C_4$ alkoxy, $C_3-C_{10}$-cycloalkyl, $C_5-C_{12}$-cycloalkenyl, phenyl, naphthyl, indenyl, tetralinyl, decalinyl, adamantyl, a monocyclic heterocyclic ring system comprising 3 to 8 atoms in the ring or a bicyclic heterocyclic ring system comprising 6 to 11 atoms, provided that at least one atom of the ring system is carbon and at least one atom of the ring system is a heteroatom selected from O, N, and S, and $R_5$ may be substituted with one or more hydroxy, nitro, $C_1-C_{10}$-alkoxy, $C_1-C_{10}$-alkyl, phenyl, $C_1-C_6$-alkylthio, nitrile, halo, $C_2-C_4$-acylamino, amino, $C_1-C_4$-dialkylamino groups; and $R_4$ is hydrogen, provided that: (1) at least one of $R_2$ and $R_3$ must be other than hydrogen; (2) when n is 2, R must be hydrogen; (3) when R is methyl and $R_3$ is hydrogen, $R_2$ cannot be methyl and (4) when R and $R_1$ are both methyl, then $R_2$ is hydrogen or methyl and n is 1.

EPO 435 503 A1 is directed to alkylated and acylated glycopeptides of the formula:

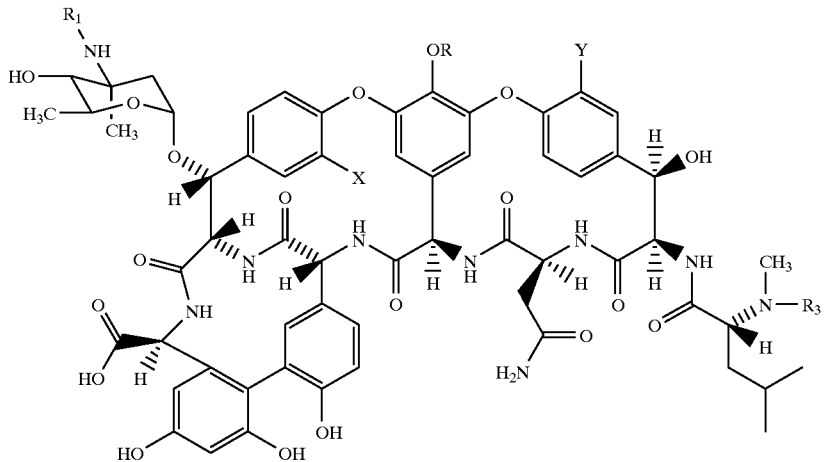

wherein:

R is hydrogen or a (4-epi-vancosaminyl)-O-glucosyl group of formula

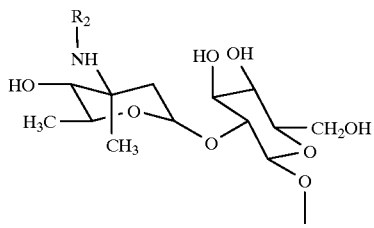

or the glucosyl group of formula

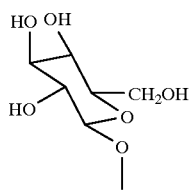

X is hydrogen or chloro;

Y is hydrogen or chloro;

$R_1$, $R_2$, and $R_3$ are independently hydrogen; $C_1$–$C_{12}$ alkyl; $C_2$–$C_9$ alkanoyl; or a group of formula

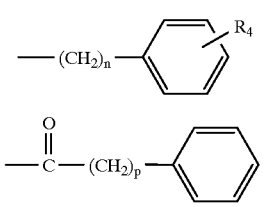

-continued

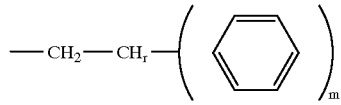

n is 1 to 3;

$R_4$ is hydrogen, halo, $C_1$–$C_8$ alkyl, $C_1$–$C_8$ alkoxy, or a group of formula

$R_5$ and $R_6$ are independently hydrogen or $C_1$–$C_3$ alkyl;

p is 0 to 2;

m is 2 or 3, and r=3−m; provided that, where R is a (4-epi-vancosaminyl)-O-glucosyl group, $R_1$, $R_2$, and $R_3$ are not all hydrogen, and where R is hydrogen or a glucosyl group, $R_1$ and $R_3$ are not both hydrogen.

Where R is (4-epi-vancosaminyl)-O-glucosyl, the glycopeptides so defined are

X=H, Y=Cl, A82846A

X=Y=Cl, A82846B

X=Y=H, A82846C

X=Cl, Y=H, orienticin A.

Thus, EPO 435 503 A1 describes alkyl derivatives of A82846A, A82846B, A82846C, and orienticin A wherein the alkyl group is

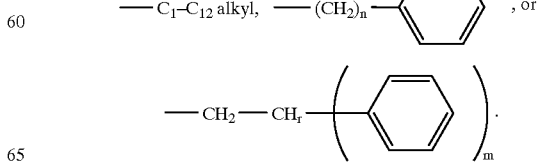

Preferred groups are $C_8$–$C_{12}$ alkyl and groups of the formula

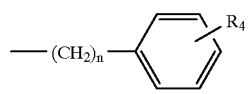

wherein $R_4$ is hydrogen, halo, $C_1$–$C_8$ alkyl, or $C_1$–$C_8$ alkoxy.

EPO 667 353 A1 describes alkylated glycopeptide antibiotics of the formula

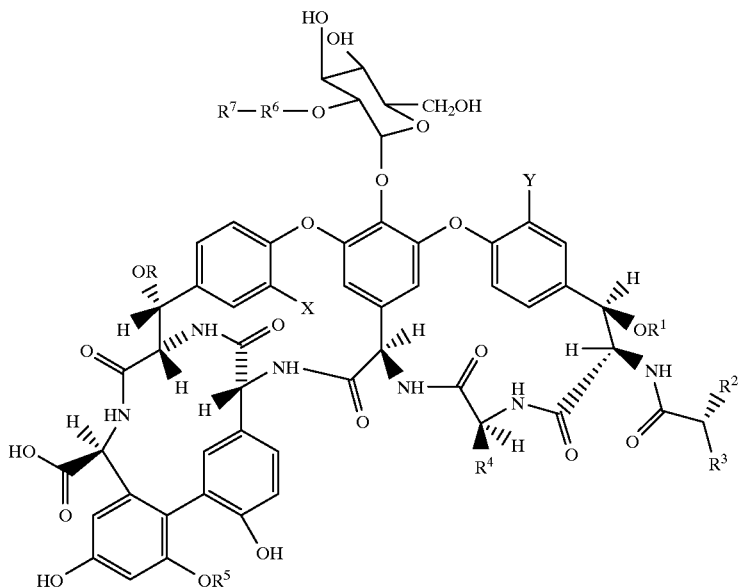

wherein:
X and Y are each independently hydrogen or chloro;
R is hydrogen, 4-epi-vancosaminyl, actinosaminyl, or ristosaminyl;
$R^1$ is hydrogen, or mannose;
$R^2$ is —$NH_2$, —$NHCH_3$, or —$N(CH_3)_2$;
$R^3$ is —$CH_2CH(CH_3)_2$, [p-OH, m-Cl]phenyl, p-rhamnose-phenyl, or [p-rhamnose-galactose]phenyl, [p-galactose-galactose]phenyl, [p-$CH_3$O-rhamnose]phenyl;
$R^4$ is —$CH_2(CO)NH_2$, benzyl, [p-OH]phenyl, or [p-OH, m-Cl]phenyl;
$R^5$ is hydrogen, or mannose;
$R^6$ is vancosaminyl, 4-epi-vancosaminyl, L-acosaminyl, L-ristosaminyl, or L-actinosaminyl;
$R^7$ is ($C_2$–$C_{16}$)alkenyl, ($C_2$–$C_{12}$)alkynyl, ($C_1$–$C_{12}$ alkyl)-$R_8$, ($C_1$–$C_{12}$ alkyl)-halo, ($C_2$–$C_6$ alkenyl)-$R_8$, ($C_2$–$C_6$ alkynyl)-$R_8$, ($C_1$–$C_{12}$ alkyl)-O—$R_8$, and is attached to the amino group of $R^6$;
$R^8$ is selected from the group consisting of:
a) multicyclic aryl unsubstituted or substituted with one or more substituents independently selected from the group consisting of:
(i) hydroxy,
(ii) halo,
(iii) nitro,
(iv) ($C_1$–$C_6$)alkyl,
(v) ($C_2$–$C_6$)alkenyl,
(vi) ($C_2$–$C_6$)alkynyl,
(vii) ($C_1$–$C_6$)alkoxy,
(viii) halo-($C_1$–$C_6$)alkyl,
(ix) halo-($C_1$–$C_6$)alkoxy,
(x) carbo-($C_1$–$C_6$)alkoxy,
(xi) carbobenzyloxy,
(xii) carbobenzyloxy substituted with ($C_1$–$C_6$)alkyl, ($C_1$–$C_6$)alkoxy, halo, or nitro,
(xiii) a group of the formula —$S(O)_{n'}$—$R^9$, wherein n' is 0–2 and $R^9$ is ($C_1$–$C_6$)alkyl, phenyl, or phenyl substituted with ($C_1$–$C_6$)alkyl, ($C_1$–$C_6$)alkoxy, halo, or nitro, and
(xiv) a group of the formula —$C(O)N(R^{10})_2$ wherein each $R^{10}$ substituent is independently hydrogen, ($C_1$–$C_6$)-alkyl, ($C_1$–$C_6$)-alkoxy, phenyl, or phenyl substituted with ($C_1$–$C_6$)-alkyl, ($C_1$–$C_6$)-alkoxy, halo, or nitro;
b) heteroaryl unsubstituted or substituted with one or more substituents independently selected from the group consisting of:
(i) halo,
(ii) ($C_1$–$C_6$)alkyl,
(iii) ($C_1$–$C_6$)alkoxy,
(iv) halo-($C_1$–$C_6$)alkyl,
(v) halo-($C_1$–$C_6$)alkoxy,
(vi) phenyl,
(vii) thiophenyl,
(viii) phenyl substituted with halo, ($C_1$–$C_6$)alkyl, ($C_2$–$C_6$)alkenyl, ($C_2$–$C_6$)alkynyl, ($C_1$–$C_6$)alkoxy, or nitro,
(ix) carbo-($C_1$–$C_6$)alkoxy,
(x) carbobenzyloxy,
(xi) carbobenzyloxy substituted with ($C_1$–$C_6$)alkyl, ($C_1$–$C_6$) alkoxy, halo, or nitro,
(xii) a group of the formula —$S(O)_{n'}$—$R^9$, as defined above,
(xiii) a group of the formula —$C(O)N(R^{10})_2$ as defined above, and
(xiv) thienyl;

c) a group of the formula:

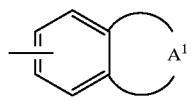

wherein $A^1$ is —OC$(A^2)_2$-C$(A^2)_2$-O—, —O—C$(A^2)_2$-O—, —C$(A^2)_2$-O—, or —C$(A^2)_2$-C$(A^2)_2$-C$(A^2)_2$-, and each $A^2$ substituent is independently selected from hydrogen, $(C_1-C_6)$-alkyl, $(C_1-C_6)$alkoxy, and $(C_4-C_{10})$cycloalkyl;

d) a group of the formula:

wherein
p is from 1 to 5; and
$R^{11}$ is independently selected from the group consisting of:
(i) hydrogen,
(ii) nitro,
(iii) hydroxy,
(iv) halo,
(v) $(C_1-C_8)$alkyl,
(vi) $(C_1-C_8)$alkoxy,
(vii) $(C_9-C_{12})$alkyl,
(viii) $(C_2-C_9)$alkynyl,
(ix) $(C_9-C_{12})$alkoxy,
(x) $(C_1-C_3)$alkoxy substituted with $(C_1-C_3)$alkoxy, hydroxy, halo$(C_1-C_3)$alkoxy, or $(C_1-C_4)$alkylthio,
(xi) $(C_2-C_5)$alkenyloxy,
(xii) $(C_2-C_{13})$alkynyloxy
(xiii) halo-$(C_1-C_6)$alkyl,
(xiv) halo-$(C_1-C_6)$alkoxy,
(xv) $(C_2-C_6)$alkylthio,
(xvi) $(C_2-C_{10})$alkanoyloxy,
(xvii) carboxy-$(C_2-C_4)$alkenyl,
(xviii) $(C_1-C_3)$alkylsulfonyloxy,
(xix) carboxy-$(C_1-C_3)$alkyl,
(xx) N-[di$(C_1-C_3)$-alkyl]amino-$(C_1-C_3)$alkoxy,
(xxi) cyano-$(C_1-C_6)$alkoxy, and
(xxii) diphenyl-$(C_1-C_6)$alkyl,
with the proviso that when $R^{11}$ is $(C_1-C_8)$alkyl, $(C_1-C_8)$alkoxy, or halo, p must be greater or equal to 2, or when $R^7$ is $(C_1-C_3$ alkyl)-$R^8$ then $R^{11}$ is not hydrogen, $(C_1-C_8)$alkyl, $(C_1-C_8)$alkoxy, or halo;

e) a group of the formula:

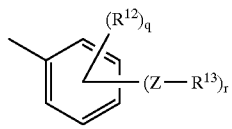

wherein
q is 0 to 4;
$R^{12}$ is independently selected from the group consisting of:
(i) halo,
(ii) nitro,
(iii) $(C_1-C_6)$alkyl,
(iv) $(C_1-C_6)$alkoxy,
(v) halo-$(C_1-C_6)$alkyl,
(vi) halo-$(C_1-C_6)$alkoxy, and
(vii) hydroxy, and
(vii) $(C_1-C_6)$thioalkyl;
r is 1 to 5; provided that the sum of q and r is no greater than 5;
Z is selected from the group consisting of:
(i) a single bond,
(ii) divalent $(C_1-C_6)$alkyl unsubstituted or substituted with hydroxy, $(C_1-C_6)$alkyl, or $(C_1-C_6)$alkoxy,
(iii) divalent $(C_2-C_6)$alkenyl,
(iv) divalent $(C_2-C_6)$alkynyl, or
(v) a group of the formula —$(C(R^{14})_2)_s$-$R^{15}$- or -$R^{15}$—$(C(R^{14})_2)_s$-, wherein s is 0–6; wherein each $R^{14}$ substituent is independently selected from hydrogen, $(C_1-C_6)$-alkyl, or $(C_4-C_{10})$ cycloalkyl; and $R^{15}$ is selected from —O—, —S—, —SO—, —SO$_2$—, —SO$_2$—O—, —C(O)—, —OC(O)—, —C(O)O—, —NH—, —N$(C_1-C_6$ alkyl)-, and —C(O)NH—, —NHC(O)—, N=N;
$R^{13}$ is independently selected from the group consisting of:
(i) $(C_4-C_{10})$heterocyclyl,
(ii) heteroaryl,
(iii) $(C_4-C_{10})$cycloalkyl unsubstituted or substituted with $(C_1-C_6)$alkyl, or
(iv) phenyl unsubstituted or substituted with 1 to 5 substituents independently selected from: halo, hydroxy, nitro, $(C_1-C_{10})$ alkyl, $(C_1-C_{10})$alkoxy, halo-$(C_1-C_3)$alkoxy, halo-$(C_1-C_3)$alkyl, $(C_1-C_3)$ alkoxyphenyl, phenyl, phenyl-$(C_1-C_3)$alkyl, $(C_1-C_6)$alkoxyphenyl, phenyl-$(C_2-C_3)$alkynyl, and $(C_1-C_6)$alkylphenyl;

f) $(C_4-C_{10})$cycloalkyl unsubstituted or substituted with one or more substituents independently selected from the group consisting of:
(i) $(C_1-C_6)$alkyl,
(ii) $(C_1-C_6)$alkoxy,
(iii) $(C_2-C_6)$alkenyl,
(iv) $(C_2-C_6)$alkynyl,
(v) $(C_4-C_{10})$cycloalkyl,
(vi) phenyl,
(vii) phenylthio,
(viii) phenyl substituted by nitro, halo, $(C_1-C_6)$ alkanoyloxy, or carbocycloalkoxy, and
(ix) a group represented by the formula -Z-$R^{13}$ wherein Z and $R^{13}$ are as defined above; and g) a group of the formula:

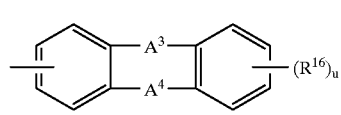

wherein
$A^3$ and $A^4$ are each independently selected from
(i) a bond,
(ii) —O—,
(iii) —S(O)$_t$—, wherein t is 0 to 2,
(iv) —C$(R^{17})_2$-, wherein each $R^{17}$ substituent is independently selected from hydrogen, $(C_1-C_6)$ alkyl, hydroxy, $(C_1-C_6)$alkyl, $(C_1-C_6)$alkoxy, or both $R^{17}$ substituents taken together are O,
(v) —N$(R^{18})_2$-, wherein each $R^{18}$ substituent is independently selected from hydrogen; $(C_1-C_6)$ alkyl; $(C_2-C_6)$alkenyl; $(C_2-C_6)$alkynyl; $(C_4-C_{10})$ cycloalkyl; phenyl; phenyl substituted by nitro, halo, $(C_1-C_6)$alkanoyloxy; or both $R^{18}$ substituents taken together are $(C_4-C_{10})$cycloalkyl;

$R^{16}$ is $R^{12}$ or $R^{13}$ as defined above; and u is 0–4.

In this reference, preferred glycopeptide antibiotics are A82846A, A82846B, A82846C, and orienticin A; preferred alkyls are those wherein $R^7$ is $CH_2-R_8$; and preferred $R^8$ moieties are those defined as groups "(d)" and "(e)".

The present invention can be utilized to make the alkylated glycopeptides described in these references. Preferred alkylated glycopeptides which can be prepared by the present process include the following:

$N^4$-n-octylA82846B
$N^4$-n-decylA82846B
$N^4$-benzylA82846B
$N^4$-(p-chlorobenzyl)A82846B
$N^4$-(p-bromobenzyl)A82846B
$N^4$-(p-propylbenzyl)A82846B
$N^4$-(p-isopropylbenzyl)A82846B
$N^4$-(p-butylbenzyl)A82846B
$N^4$-(p-isobutylbenzyl)A82846B
$N^4$-(p-pentylbenzyl)A82846B
$N^4$-(p-isohexylbenzyl)A82846B
$N^4$-(p-octylbenzyl)A82846B
$N^4$-(p-propoxybenzyl)A82846B
$N^4$-(p-isopropoxybenzyl)A82846B
$N^4$-(p-butoxybenzyl)A82846B
$N^4$-(p-tert-butoxybenzyl)A82846B
$N^4$-(p-pentyloxybenzyl)A82846B
$N^4$-(p-hexyloxybenzyl)A82846B
$N^4$-(o-hexyloxybenzyl)A82846B
$N^4$-(p-heptyloxybenzyl)A82846B
$N^4$-(p-octyloxybenzyl)A82846B
$N^4$-phenethylA82846B
$N^4$-(4-phenylbenzyl)A82846B
$N^4$-(4-(4-chlorophenyl)benzylA82846B
$N^4$-(4-(4-methylbenzyloxy)benzyl)A82846B
$N^4$-(4-(4-ethylbenzyloxy)benzyl)A82846B
$N^4$-(4-(4-chlorophenethyl)benzyl)A82846B
$N^4$-(4-(2-(4-methoxyphenyl)ethynyl)benzyl)A82846B.

The references noted above describe the reductive alkylation as comprising a first step, in which the glycopeptide is reacted with the respective aldehyde or ketone to form a Schiff's base, which in a second step is reduced to the desired alkylated product. In one variation of this procedure, EPO 667 353 A1 describes a process in which the reducing agent is added simultaneously with the glycopeptide and aldehyde or ketone.

The references suggest a strong preference for sodium cyanoborohydride as reducing agent. While sodium cyanoborohydride is a successful reagent for small scale use, its use in large scale production is less satisfactory. This is due to safety and environmental issues posed by the cyanide ion. Accordingly, sodium cyanoborohydride is less than an ideal reducing agent for larger scale reactions.

Reducing agents are legion, but many are unsatisfactory for the glycopeptides. One of the many reducing agents known for use in reductive alkylations is pyridine.borane (see *J. Chem Soc. Perkin Trans.* 1 (1984), pages 717–720, which is incorporated herein by reference). It has now been discovered that pyridine.borane is a uniquely acceptable reagent for alkylative reductions on glycopeptides, while presenting no safety or environmental hazards as is the case with sodium cyanoborohydride. Furthermore, in a preferred embodiment, it has been discovered that portionwise addition of the pyridine.borane increases yields.

Thus, the present invention is directed to an improved process for reductively alkylating an amine-containing glycopeptide antibiotic, which process comprises reacting the glycopeptide antibiotic with an aldehyde or ketone in the presence of a reducing agent, wherein the improvement comprises employing pyridine.borane as reducing agent. In a preferred embodiment, the glycopeptide antibiotic, aldehyde or ketone, and a portion of the reducing agent are mixed together at the same time, and one or more additional portions of reducing agent are added thereafter.

In carrying out the present invention, standard conditions for reductive alkylations of glycopeptides are employed, other than the identity of the reducing agent and the preference for its portionwise addition. Thus, the glycopeptide and aldehyde or ketone are initially dissolved in a solvent which is at least predominantly methanol, and which is preferably only methanol. If only these reagents are supplied, some small amount of Schiff's base is produced, but the reaction equilibrium does not favor complete production of the Schiff's base. Addition of reducing agent shifts the equilibrium as Schiff's base is converted to alkylated product. As noted, EPO 667 353 A1 teaches a preference for simultaneous addition of the reducing agent with the glycopeptide antibiotic and aldehyde or ketone. Thus, in the present invention, the glycopeptide, aldehyde or ketone, and pyridine.borane are added at essentially the same time.

Further, it has been discovered that when employing pyridine.borane as reducing agent, even simultaneous addition of glycopeptide antibiotic, aldehyde or ketone, and reducing agent leads to only modest yields and that such yields can be increased by portionwise addition of the pyridine.borane, with no more than a portion being added initially to the glycopeptide antibiotic and the aldehyde or ketone.

The exact number and timing of portions is not critical. The reaction is generally conducted over a period of time from 4 to 48 hours and preferably from 6 to 24 hours. In the preferred practice of the present invention, a first portion of pyridine.borane is added with the glycopeptide antibiotic and aldehyde or ketone, and the remainder of the pyridine.borane is added in one, two, or more subsequent portions. The ideal sequence of pyridine.borane addition appears to be five portions at 2 to 4 hour intervals (counting the initial addition as the first of the five). Devices can be employed to provide a continuous delivery of the pyridine.borane.

In another preferred embodiment of the invention, a source of soluble copper is supplied to the reaction mixture, initially converting the glycopeptide to a copper complex, which becomes the reactive entity. The use of copper confers regioselectivity of reaction in those glycopeptides having multiple reactive amines. For example, in A82846B, the use of copper minimizes reaction on the $N^1$ (leucine) site and on the $N^6$ (monosaccharide) site, thereby providing higher yields of the product monoalkylated on the $N^4$ (disaccharide) amine.

The identity of the copper source is not critical, so long as it is at least partially soluble and does not negatively impact the pH. Suitable copper salts are cupric acetate, cupric trifluoroacetate, cupric cyclohexanebutyrate, cupric 2-ethylhexanoate, cuprous chloride, cupric chloride, and cupric bromide. A preferred source of copper is copper (II) acetate, most conveniently employed as the hydrate.

The reaction should be conducted at a pH of 6–8, and preferably at a pH of 6.3–7.0.

The amounts of reactants and reagents to be employed are not critical; amounts to maximize the yield of product will vary somewhat with the identity of the reactants. The reaction consumes the glycopeptide antibiotic and the aldehyde or ketone in equimolar amounts. A slight excess of the aldehyde or ketone, e.g., 1.3 to 1.7:1, is preferred. The amount of the glycopeptide antibiotic to be used must be corrected for its purity. The reaction consumes an equimolar amount of the pyridine.borane. A slight excess is preferable. The amount of soluble copper, if used, is important. The process first results in the formation of a 1:1 copper complex with the glycopeptide antibiotic. Therefore, the copper is preferably present in an amount approximately equimolar with the glycopeptide antibiotic. However, amounts exceeding one molar equivalent are undesirable because excess copper decomposes the pyridine.borane.

Summarizing the foregoing, the ideal amounts to be employed are a ratio of: glycopeptide:aldehyde or ketone:reducing agent:copper salt of: 1:1.3 to 1.7:1.5:0.9 to 1.

The concentration of the reactants in the solvent has some bearing on the process. Methanol volume relative to mass of glycopeptide antibiotic can vary from 50:1 to 500:1; a 100:1 dilution appears to be a useful, practical ratio, although higher dilutions may give slightly higher yields.

The temperature at which the process is carried out is important. Reaction mixtures in methanol boil at about 67° C., thereby setting the maximum temperature when employing straight methanol as the solvent. Higher temperatures are of course possible when employing mixtures of methanol or when operating under pressure. Lower temperatures can be tolerated, but preferably not lower than about 45° C. The ideal conditions depend upon whether or not copper is employed in the reaction. When copper is not added, it is preferred to conduct the reaction in straight methanol at temperatures of about 58–67° C. When employing copper, it is important to conduct the reaction at slightly lower temperatures of about 58–63° C.; again, straight methanol is preferred.

Upon the completion of the reaction, the reaction mixture is preferably quenched, as by the addition of sodium borohydride. This reagent consumes residual aldehyde or ketone and thereby prevents further undesired reactions.

The product is isolated from the reaction mixture in conventional manner. When copper has been employed, the product is isolated from the reaction mixture as a copper complex of the alkylated glycopeptide. Isolation is achieved by concentration of the reaction mixture and precipitation of the complex by addition of an antisolvent such as ethyl acetate, acetone, 1-propanal, isopropyl alcohol, or preferably acetonitrile. The complex can be broken by aqueous treatment at pH $^2$4, freeing the simple alkylated glycopeptide product, which can, if desired, be purified in conventional manner.

The following examples illustrate the present invention and will enable those skilled in the art to practice the same.

EXAMPLE 1

A82846B (0.50 g, 84.3% potency, 0.42 bg, 0.26 mmol) was stirred in 50 mL methanol and 4'-chloro-4-biphenylcarboxaldehyde (72 mg, 0.33 mmol) and pyridine.borane complex (0.033 mL, 0.33 mmol) were added. The mixture was heated at reflux for 6 hours before being cooled to ambient temperature. HPLC analysis of a reaction aliquot afforded a yield of 0.25 g (53.2%) of $N^4$-(4-(4-chlorophenyl)benzyl)A82846B.

EXAMPLE 2

Portionwise Addition of Pyridine.Borane

A82846B (0.50 g, 83.9% potency, 0.26 mmol) and 4'-chloro-4-biphenylcarboxaldehyde (98 mg, 0.45 mmol) were stirred in 50 mL methanol and pyridine.borane complex (0.015 mL, 0.15 mmol) was added. The reaction mixture was heated at reflux for 4 hours and an additional aliquot of pyridine.borane complex (0.015 mL, 0.15 mmol) was added. After heating at reflux for 4 hours longer a final addition of pyridine.borane complex (0.015 mL, 0.15 mmol) was made. The reaction mixture was heated at reflux for another 20 hours. After cooling to ambient temperature HPLC analysis of a reaction aliquot afforded a yield of 0.27 g (58.0%) of $N^4$-(4-(4-chlorophenyl)benzyl)A82846B.

EXAMPLE 3

With Copper

A82846B (0.50 g, 84.3% potency, 0.42 bg, 0.26 mmol) was stirred in 50 mL methanol and cupric acetate (45 mg, 0.25 mmol) was added. After stirring at ambient temperature for 10 min, 4'-chloro-4-biphenylcarboxaldehyde (84 mg, 0.39 mmol) and pyridine.borane complex (0.039 mL, 0.39 mmol) were added. The mixture was heated at 57° C. for 24 hours before being cooled to ambient temperature. HPLC analysis of a reaction aliquot afforded a yield of 0.34 g (72.3%) of $N^4$-(4-(4-chlorophenyl)benzyl)A82846B.

EXAMPLE 4

With Copper+Portionwise Addition of Pyridine.Borane

A82846B (0.50 g, 76.3% potency, 0.38 bg, 0.24 mmol) and cupric acetate monohydrate (43 mg, 0.216 mmol) were stirred in 50 mL methanol and 4'-chloro-4-biphenylcarboxaldehyde (84.5 mg, 0.39 mmol) and pyridine.borane complex (0.011 mL, 0.11 mmol) were added. The mixture was heated at 63° C. for 2 hours and an additional portion of pyridine.borane was added (0.01 mL, 0.1 mmol). After 2 hours more at 63° C. a third portion of pyridine.borane (0.005 mL, 0.05 mmol) was added. A fourth portion of pyridine.borane (0.005 mL, 0.05 mmol) was added 2 hours later followed by a fifth portion of pyridine.borane (0.005 mL, 0.05 mmol) after another 5 hours at 63° C. The mixture was heated at 63° C. for another 11 hours before being cooled to ambient temperature. HPLC analysis of a reaction aliquot afforded a yield of 0.34 g (79.2%) of $N^4$-(4-(4-chlorophenyl)benzyl)A82846B.

The reactions reported in Examples 1, 3, and 4 were also evaluated (1) for the amount of the remaining starting glycopeptide, (2) for the amount of products alkylated on amine sites other than the $N^4$-position, and (3) for the amount of multiply-alkylated products. The results are set forth in the following table and are expressed as a percentage relative to the intended product monoalkylated on the $N^4$-amine; yields of the intended product are actual yields as recited in the foregoing examples.

TABLE I

| Ex. No. | % Mono-alkylated at $N^4$ | % A82846B | % Mono-alkylated at $N^6$ | % Mono-alkylated at $N^1$ | % Di-alkylated at both $N^4$ and $N^6$ | % Di-alkylated at both $N^1$ and $N^4$ | % Tri-alkylated |
|---|---|---|---|---|---|---|---|
| 1 | 53.2 | 47.6 | 9.9 | 1.3 | 21.7 | 7.8 | 1.8 |
| 3 | 72.3 | 17.8 | 2.1 | 0.7 | 6.2 | 2.5 | 0.4 |
| 4 | 79.2 | 9.2 | 1.4 | 0.3 | 7.4 | 3.4 | 0.3 |

These data show that portionwise addition of pyridine.borane, accompanied by the use of copper, maximizes yields of the product monoalkylated on $N^4$, while minimizing yields of other alkylated products.

EXAMPLE 5

With Copper+Portionwise Addition of Pyridine.Borane by Syringe Pump

A82846B (0.50 g, 83.4% potency, 0.26 mmol) and cupric acetate (47 mg, 0.26 mmol) were stirred in 50 mL methanol and 4'-chloro-4-biphenylcarboxaldehyde (98 mg, 0.45 mmol) and pyridine.borane complex (0.015 mL, 0.15 mmol) were added. The reaction mixture was heated at 63° C. for 2 hours. Additional pyridine.borane complex (0.03 mL, 0.30 mmol) in 2 mL methanol was added to the reaction mixture at a rate of 400 uL/hour using a syringe pump. The temperature was maintained at 63° C. during the addition. After the addition was complete, heating was continued to afford a total reaction time of 24 hours. After cooling to ambient temperature, HPLC analysis of a reaction aliquot afforded a yield of 0.35 g (74.3%) of $N^4$-(4-(4-chlorophenyl)benzyl) A82846B.

The following HPLC System was used for in situ reaction monitoring and yield calculation: HPLC system Waters 600E with HP3395 integrator and Applied Biosystems 757 detector set at 230 nm, sensitivity 0.1 absorption units, 1 sec. filter rise time. Column: DuPont Zorbax SB-Phenyl, 4.6 mm×25 cm. Eluant A: 10% acetonitrile, 90% buffer (0.2% triethylamine, 0.25% $H_3PO_4$). Eluant B: 60% acetonitrile, 40% buffer (0.2% triethylamine, 0.25% $H_3PO_4$). Gradient profile at 1 mL/min: initialize 100% A, gradient to 80% A, 20% B over 5 minutes, hold 5 minutes, gradient to 100% B over 20 minutes, gradient to 100% A over 5 minutes, hold 20 minutes. Sample preparation: 0.5–1.0 g of reaction mixture diluted to 25 mL in acetonitrile - buffer. Hold at ambient temperature about 30 minutes until the purple color of the copper complex is discharged. The desired glycopeptide alkylation product elutes at 16–18 minutes, the starting glycopeptide nucleus at 3–4 minutes, the site $N^6$ (monosugar) alkylation product at 18–19 minutes, the site $N^1$ (methyl leucine) alkylation product at 19–21 minutes, dialkylated impurities at 24–26 minutes, and aldehyde at 35–36 minutes. In situ yield is determined by correlation to standards prepared with a reference sample of the product.

We claim:

1. A process for reductively alkylating an amine-containing glycopeptide antibiotic comprising (i) mixing the amine-containing glycopeptide antibiotic, an aldehyde or ketone, a pyridine.borane reducing agent and a source of soluble copper to form a mixture, wherein the reducing agent is added in one or more portions.

2. The process of claim 1 wherein the glycopeptide antibiotic is vancomycin, A82846B, A82846B, A82846C, or orienticin A.

3. The process of claim 1 wherein the glycopeptide antibiotic is A82846B.

4. The process of claim 1 wherein the aldehyde is 4'-chloro-4-biphenylcarboxyaldehyde.

5. The process of claim 1 wherein the reducing agent is added in five portions at 2 to 4 hour intervals.

6. The process of claim 1 wherein the soluble source of copper is selected from the group consisting of cupric acetate, cupric trifluoroacetate, cupric cyclohexanebutyrate, cupric 2-ethylhexanoate, cuprous chloride, cupric chloride, and cupric bromide.

7. The process of claim 1 wherein the source of soluble copper is a hydrate of copper (II) acetate.

8. The process of claim 1 wherein the source of soluble copper is present in an amount approximately equimolar with the glycopeptide antibiotic.

9. The process of claim 1 wherein the amounts of the glycopeptide antibiotic and the source of soluble copper are present at a ratio of 1:0.9 to 1 glycopeptide antibiotic:source of soluble copper.

10. The process of claim 1 wherein said process is carried out in methanol at 58–63° C.

11. The process of claim 1 further comprising step (ii) adding sodium borohydride.

12. A process for reductively alkylating an amine-containing glycopeptide antibiotic comprising (i) mixing the amine-containing glycopeptide antibiotic, an aldehyde or ketone, and a first portion of pyridine.borane reducing agent to form a mixture; and (ii) adding one or more subsequent portions of the reducing agent to the mixture.

* * * * *